United States Patent [19]
Banks

[11] Patent Number: 4,840,616
[45] Date of Patent: Jun. 20, 1989

[54] SYRINGE HYPODERMIC NEEDLE

[75] Inventor: Gilbert H. Banks, Rainbow Flats, Australia

[73] Assignee: Bev-Cap Plastics Pty. Ltd., New South Wales, Australia

[21] Appl. No.: 161,574

[22] Filed: Feb. 29, 1988

[51] Int. Cl.⁴ .............................................. A61M 5/00
[52] U.S. Cl. .................................. 604/110; 604/218; 604/210
[58] Field of Search ............... 604/110, 210, 208, 220, 604/187, 207, 218

[56] References Cited
U.S. PATENT DOCUMENTS

| | | | |
|---|---|---|---|
| 2,869,541 | 1/1959 | Helmer et al. | 604/210 |
| 2,875,761 | 3/1959 | Helmer et al. | 604/210 |
| 4,643,199 | 2/1987 | Jennings, Jr. et al. | 604/110 |
| 4,650,468 | 3/1987 | Jennings, Jr. | 604/110 |
| 4,654,035 | 3/1987 | Ando | 604/210 |

Primary Examiner—John D. Yasko
Attorney, Agent, or Firm—Townsend and Townsend

[57] ABSTRACT

A single use disposable medical syringe with the plunger shaft having first and second splines. The first splint co-acts with a first pawl to allow withdrawal only of the plunger. The plunger is then rotated to another position, wherein the second spline co-acts with a second pawl to permit insertion only of the plunger. The plunger may not then be withdrawn for re-use.

9 Claims, 2 Drawing Sheets

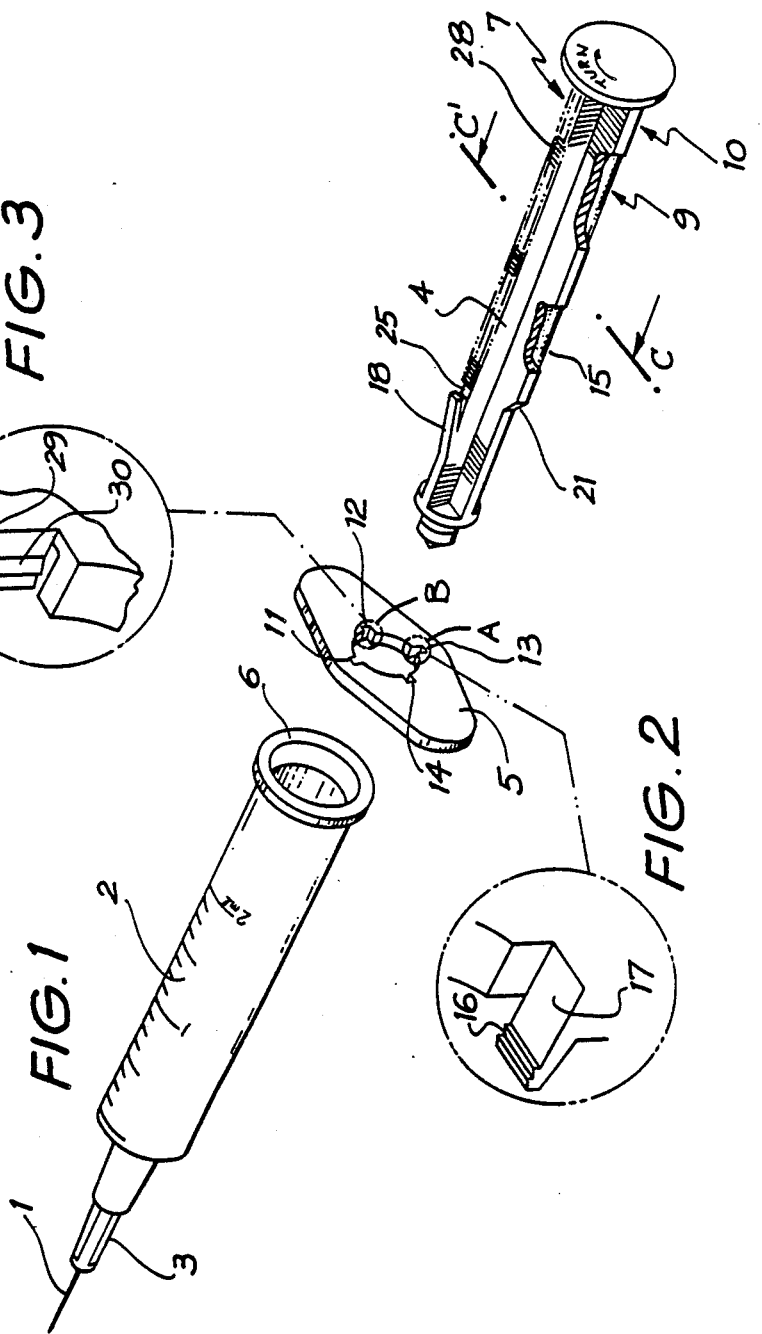

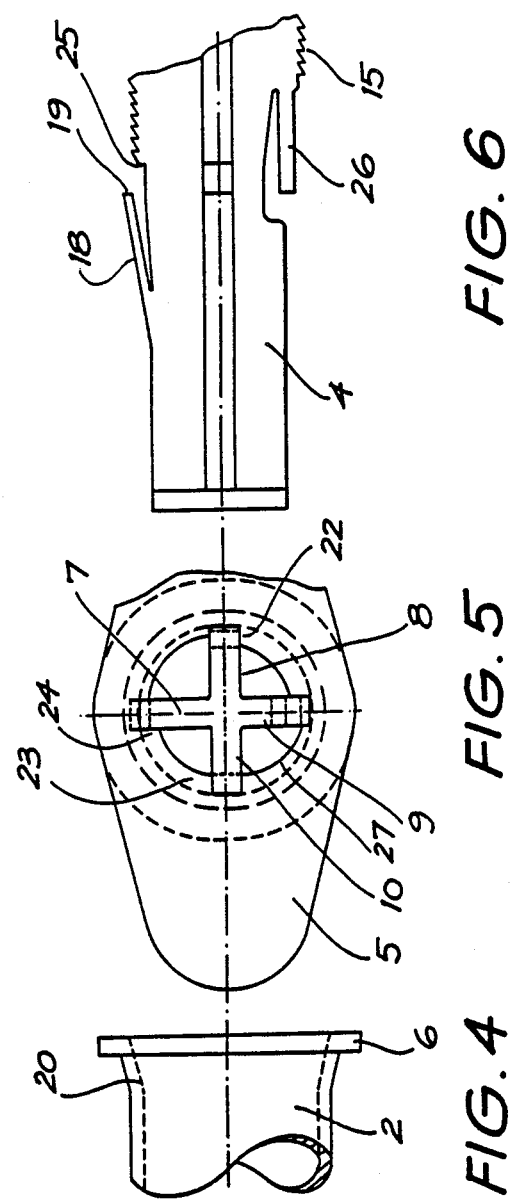

SYRINGE HYPODERMIC NEEDLE

The present invention relates to the field of medical syringe and in particular to an improved single use disposable syringes and to a disposable unitary syringe/hypodermic needle combination.

Hypodermic needles for injecting fluids into the human body are extensively used by hospitals and the medical profession in order to administer drugs although such hypodermic needles are additionally utilised by drug addicts to administer illegal drugs.

In all instances it is only intended that a hypodermic needle be utilised once. This is due to the fact that a hypodermic needle is supplied in a sterile condition from the manufacturer and after one use this sterile condition no longer exists and the hypodermic needle should be discarded. Traditionally hypodermic needles are fitted to the end of a syringe and the needle may be supplied with or without an associated syringe.

Until recently the supply of needles has been restricted in order to try and inhibit the use of illegal drugs. As a consequence, drug addicts frequenty re-use needles thereby assisting the transfer of infection and disease from one person to another.

In recent years the AIDS epidemic amongst homosexuals and now the community in general has caused governments to look seriously at the problem of drug addicts re-using hypodermic needles and thereby assisting the spread of AIDS. Certain governments have proposed or implemented schemes whereby hypodermic needles are freely available through chemists or other authorised outlets although such problem has not eliminated the risk of drug addicts re-using needles due to the fact that such authorised outlets may not be open 24 hours a day or may not be sufficiently convenient at a time when the drug addict desires an injection.

It is consequently an object of the present invention to discourage the re-use of hypodermic needles by drug addicts and others in the community.

According to the present invention there is provided a single use disposable medical syringe comprising a syringe body adapted at one end to receive a hypodermic needle, a plunger located within said syringe body and passing through an end plate attached to other end of said syringe body and characterised in that:

said plunger includes a plunger head forming at any time a seal with an interior surface of said syringe body, and a plunger shaft including at least a first and second longitudinally extending spline, said first spline including teeth adapted to co-act with a first pawl and said second spline including teeth adapted to co-act with a second pawl, said splines further including circumjacent and corresponding first and second recesses;

said end plate having an aperture to locate said plunger shaft, said aperture having three or more channels each adapted to receive one or other said splines and two of said channels being provided respectively with said first and second pawls;

said recesses allowing free rotation of said plunger within said end plate aperture such that said first pawl allows withdrawal only of said plunger whereupon predetermined free rotation of said plunger engages said second pawl which allows insertion only of said plunger.

One embodiment of the present invention will not be described with reference to the accompanying drawings in which:

FIG. 1 is an exploded view of a syringe/needle in accordance with the present invention in perspective;

FIG. 2 is an enlarged partial perspective view of area A in view 1; and

FIG. 3 is a partial enlarged view of area B in FIG. 1;

FIG. 4 is a part side elevation of the body of the syringe of FIG. 1;

FIG. 5 is a section through C—C' of the plunger of FIG. 1 when the syringe is assembled; and FIG. 6 is a part side elevation of the plunger of figure 1.

The embodiment of FIG. 1 depicts hypodermic needle 1 permanently affixed to the body 2 of a syringe assembly. The mount 3 for the needle is ultrasonically welded to the body 2 in order that the needle 1, mount 3 and body 2 are unitary. The syringe assembly is provided with a plunger 4 and end plate 5, the end plate 5 being welded (not shown) to flange 6 of the body 2 when the syringe is in the assembled form.

The plunger 4 is provided with splines 7, 8, 9 and 10 (best viewed in FIG. 5) in order to govern its rotation with respect to end plate 5 and body 2, the splines being intended to lock into guide channels 11, 12, 13 and 14 in end plate 5.

The syringe is supplied with the plunger fully inserted within the body 2 and ready for withdrawal in order to charge body 2 with fluid. During the initial withdrawal, splines 7, 8, 9 and 10 co-operate with guide channels 11, 12, 13 and 14 respectively in order to ensure that no rotation of the plunger with respect to the body 2 is possible. During the initial withdrawal rachet teeth 15 on plunger 4 co-operate with corresponding teeth 16 on resilient pawl 17 as shown in figure 2. The pawl 17 is located on the inside of end plate 5 adjacent the base of channel 13. The co-operation of teeth 15 with teeth 16 ensures that at no time during the initial withdrawal of the plunger can the direction of travel of the plunger be reversed so as to eject liquid from the needle.

Once the plunger has reached its maximum point of withdrawal from the body, leaf spring 18 (best viewed in figure 6) which is biased towards an open position wherein its free end 19 is well spaced from the plunger will ride up taper 20 on the body with its free end 19 hitting the end plate 5 at a point radially outward of guide recess 11 thereby preventing further withdrawal of the plunger. Once the plunger has been withdrawn to this point (with the free end 19 of leaf spring 18 adjacent the end plate) splines 8 and 10 step radially inwardly at 21 as can be seen best in FIG. 3 so that shoulders 22 and 23 of guide channels 12 and 14 no longer prevent clockwise rotation of the plunger. Shoulder 24 of recess 11 prevents anit-clockwise rotation of the plunger whereas step 25 ensures that spline 7 is free to rotate clockwise for ninety degrees until it hits shoulder 22 of guide channel 12.

The plunger is therefore free to rotate clockwise through ninety degrees within body 2 and indeed this rotation must take placed in order to disengage rachet teeth 15 from pawl 17 in order to allow downward stroke of the plunger into the syringe body 2. During such clockwise rotation leaf spring 26 will ride up ramp 27 as shown in FIG. 5 before dropping into channel 14 thereby preventing further rotation of the plunger.

After such ninety degree rotation it will be appreciated that rachet teeth 15 are disengaged from pawl 17 but that rachet teeth 28 on spline 7 are not engaged with pawl 29 and teeth 30 forming the base of guide channel 12 and best viewed in FIG. 3. This rachet system allows the plunger to be pushed into body 2 in order to eject fluid from needle 1 but acts so as to prevent a second withdrawal of the plunger. Once the plunger has been pushed fully into the body 2 so as to eject all fluid from needle 1 the rachet system defined by teeth 28 and 30 and pawl 29 will prevent any further withdrawal of the plunger so as to re-load the syringe assembly, it is not possible to disengage this rachet system due to the fact that when the plunger is in the fully inserted position splines 7, 8, 9 and 10 are locked into guide channels 11, 12, 13 and 14. The syringe assembly is therefore totally inoperable after its one use and must be discarded.

It will be appreciated that a device in accordance with the present invention will prevent re-use of hypodermic needles due to the unitary nature of the syringe/needle combination. This unitary nature additionally ensures that if a needle is discarded carelessly then there is a high probability that it will be noticed due to the bulk of the attached syringe.

Use of needle/syringe combinations in accordance with the present invention in hospitals and other legal applications would help minimise the spread of disease through needle re-use by removing the motive for drug users and others to misappropriate discarded hospital supplies.

It should be appreciated that many non-return mechanisms may be devised for a plunger apart from those above described whilst maintaining the basic concept of the present invention.

I claim:

1. A single use disposable medical syringe comprising a syringe body adapted at one end to receive a hypodermic needle, a plunger located within said syringe body and passing through an end plate attached to other end of said syringe body and characterised in that:

said plunger includes a plunger head forming at any time a seal with an interior surface of said syringe body, and a plunger shaft including at least a first and second longitudinally extending spline, said first spline including teeth adapted to co-act with a first pawl and said second spline including teeth adapted to co-act with a second pawl, said splines further including circumjacent and corresponding first and second recesses;

said end plate having an aperture to locate said plunger shaft, said aperture having three or more channels each adapted to receive one or other said splines and two of said channels being provided respectively with said first and second pawls;

said recesses allowing free rotation of said plunger within said end plate aperture such that when said first pawl allows withdrawal only of said plunger whereupon predetermined free rotation of said plunger engages said second pawl which allows insertion only of said plunger.

2. A syringe according to claim 1 wherein the plunger has four said splines and the end plate has four channels.

3. A syringe according to claim 2 wherein two only of said splines include teeth.

4. A single use disposable medical syringe comprising a syringe body adapted at one end to receive a hypodermic needle, a plunger located within said syringe body and passing through an end plate attached to other end of said syringe body and characterised in that:

said plunger included a plunger head forming at any time a seal with an interior surface of said syringe body, and a plunger shaft including first, second, third and fourth longitudinally extending splines, said first spline including teeth adapted to co-act with a first pawl and said third spline being disposed 180° about said plunger shaft to said first spline and including teeth adapted to co-act with a second pawl, said splines further including circumjacent and corresponding first and second recesses;

said end plate having an aperture to locate said plunger shaft, said aperture having four channels each adapted to receive one or other said splines and two of said channels being provided respectively with said first and second pawls;

said recesses allowing free rotation of said plunger within said end plate aperture such that said first pawl allows withdrawal only of said plunger whereupon predetermined free rotation of said plunger engages said second pawl which allows insertion only of said plunger.

5. A syringe according to claim 4 wherein the free rotation of the plunger is 90°.

6. A syringe according to claim 5 wherein at least one of said second and fourth splines includes detent means to enable a once only predetermined free rotation.

7. A syringe according to claim 4 wherein said syringe body increases in diameter over a region proximal to said end plate and at least one said spline includes a leaf spring biased so as to open in said region of increasing body diameter and abut a face of said end plate.

8. A syringe as claimed in claim 1 with a hypodermic needle permanently affixed thereto.

9. A syringe as claimed in claim 4 with a hypodermic needle permanently affixed thereto.

* * * * *